United States Patent
Lanze et al.

(10) Patent No.: US 6,695,991 B1
(45) Date of Patent: Feb. 24, 2004

(54) DEVICE FOR EXCHANGING A DIE PLATE OF A PRILLING TOWER AND METHOD FOR THE AUTOMATIC EXCHANGE

(75) Inventors: Rolf Lanze, Krefeld (DE); Günter Holdenried, Leichlingen (DE); Rainer Neumann, Krefeld (DE); Frieder Heydenreich, Düsseldorf (DE); Tony van Osselaer, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/890,018

(22) PCT Filed: Jan. 24, 2000

(86) PCT No.: PCT/EP00/00518

§ 371 (c)(1),
(2), (4) Date: Jul. 25, 2001

(87) PCT Pub. No.: WO00/45946

PCT Pub. Date: Aug. 10, 2000

(30) Foreign Application Priority Data

Feb. 4, 1999 (DE) .......................................... 199 04 407

(51) Int. Cl.⁷ ................................................. B29B 9/10
(52) U.S. Cl. .............................................. 264/13; 425/6
(58) Field of Search ................................ 264/13; 425/6

(56) References Cited

U.S. PATENT DOCUMENTS 4,220,441 A     9/1980  Tomita et al. ................. 425/6

FOREIGN PATENT DOCUMENTS

JP           6-107581          4/1994

OTHER PUBLICATIONS

Patent Abstracts of Japan, vol. 018, No. 385 (C–1227), Jul. 20, 1994, & JP 06 107561 A (Nippon Steel Chem. Co. Ltd.), Apr. 19, 1994.

*Primary Examiner*—Mary Lynn Theisen
(74) *Attorney, Agent, or Firm*—Joseph C. Gil; Aron Preis; James R. Franks

(57) ABSTRACT

A device for exchanging a die plate of a molten bisphenol A prilling tower is described. The device comprises: (a) at least two die plates; (b) a guide which is in contact with the die plates; and (c) a drive mechanism, wherein the drive mechanism moves the die plates linearly and serially between an operating position and an exchange position along the guide. Also described is a process of automated operation of the device at the top of a bisphenol A prilling tower.

12 Claims, 3 Drawing Sheets

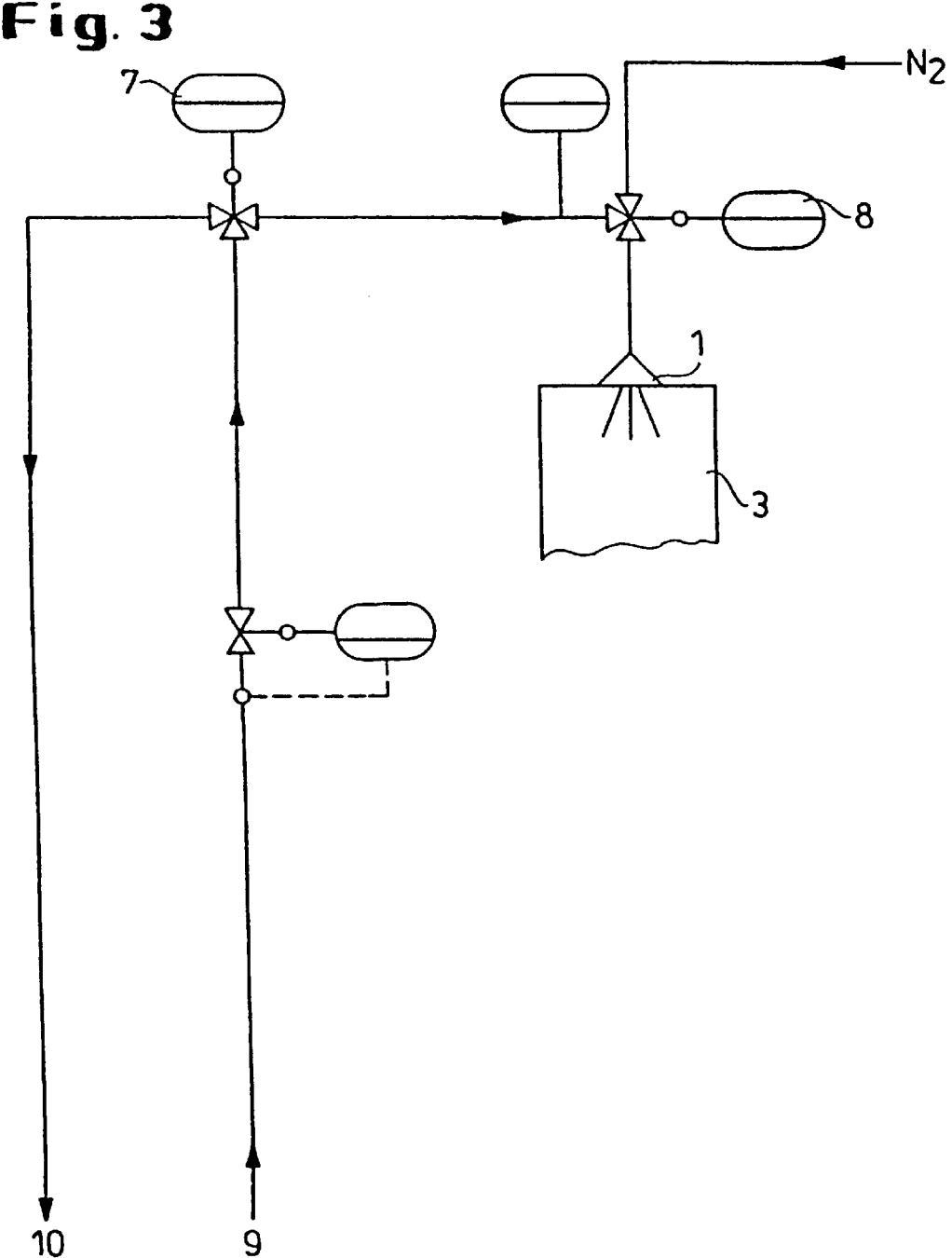

DEVICE FOR EXCHANGING A DIE PLATE OF A PRILLING TOWER AND METHOD FOR THE AUTOMATIC EXCHANGE

CROSS REFERENCE TO RELATED PATENT APPLICATIONS

The present patent application claims the right of priority under 35 U.S.C. 119 (a)–(d) and 35 U.S.C. 365 of International Application No. PCT/EP00/00518, filed Jan. 24, 2000, which was published in German as International Patent Publication No. WO 00/45946 on Aug. 10, 2000, which is entitled to the right of priority of German Patent Application No. 199 04 407.4, filed Feb. 4, 1999.

FIELD OF THE INVENTION

The invention relates to a device for exchanging a die plate of a prilling tower, wherein molten bisphenol A is introduced into the prilling tower through a plurality of dies located in the die plate and is cooled to room temperature with a view to the production of prills, and also to a process for automated exchange by means of such a device.

BACKGROUND OF THE INVENTION

Bisphenols are chemical compounds with two phenol groups, obtained by causing phenol to react with ketones, whereby bisphenol A (2,2-bis(4-hydroxyphenyl)propane) is formed as a result of the reaction of phenol and acetone. Bisphenol A is processed further into epoxy resins, polycarbonates and polysulfones. With a view to facilitating filling, transport and storage, granular material, flakes or prills are produced from a bisphenol melt by cooling, whereby prills present advantages over granular material or flakes by reason of their lower proportion of dust and better flow properties.

A process for producing bisphenol A prills is known from JP-6-107 581, wherein molten bisphenol A is charged in the top region of a prilling tower and cooling gas, which abstracts the heat of fusion from the falling droplets of melt, is introduced in counter-flow at the bottom of the prilling tower. The solidified prills are removed at the bottom of the prilling tower.

Charging of the bisphenol melt in the top of the prilling tower is effected in this case by means of a die plate which is arranged on the top of the prilling tower. With a view to uniform distribution of the bisphenol melt, the die plate is preferably spherically domed. In the die plate a plurality of bores is uniformly distributed on the surface of the die plate.

SUMMARY OF THE INVENTION

The object underlying the invention is therefore to create a device for exchanging such a die plate that enables the initial pressure of the die plate to be maintained within a defined range for variable load ranges of a prilling tower. Moreover, it is desirable that the die-exchanging device can be operated automatically from outside and causes no unnecessary stoppage times of the prilling tower in the event of a change of the load range.

With regard to the device, the object is achieved in that at least two die plates are provided that are capable of being brought in linear manner along a guide into an operating position or an exchange position by means of a suitable drive mechanism. As regards the process, the object is achieved by virtue of the following steps:

redirection of the bisphenol melt from the prilling tower into the melt container, feeding of nitrogen into the prilling tower over a predetermined period, relaxation of the pressure in the prilling tower, release of the contact pressure on the die plate, actuation of the displacement cylinder with a view to displacing a die plate from the exchange position into the operating position, application of contact pressure onto the die plate, feeding of nitrogen into the prilling tower over a predetermined period and redirection of the bisphenol melt from the melt container into the prilling tower.

BRIEF DESCRIPTION OF THE DRAWINGS

FIG. 3 is a schematic diagram of the feeding of melt for the purpose of elucidating the exchange operation of the die-exchanging device.

DETAILED DESCRIPTION OF THE INVENTION

In order to create a particularly high degree of flexibility in the course of the production of prills, working takes place with differing die plates, depending on various throughputs, which each comprise a different number and/or distribution of through bores. In this way an automatic adaptation to the load is achieved. At the same time it is possible that, through the choice of the suitable die plate, load ranges from 0.5 to 8 t of bisphenol melt per hour are possible without departing from an initial pressure of the die plate within a previously defined range from, preferably, 0.1 to 0.3 bar.

In further development of the invention, slide rails that have a length of at least twice the die-plate length, preferably four times the die-plate length, are provided for the guidance of the die plates.

With a view to improving the exchange operation, the slide rails consist, at least on their surface, of a copper bronze, preferably a $CuSn_8$ alloy. This alloy is reliably resistant to bisphenol vapours.

A further development of the invention provides that the slide rails and/or the die plates exhibit a polished surface on their contact region. Here a depth of roughness of 0.8 $\mu$m has proved particularly expedient.

By way of drive mechanism for displacing the die plate, according to a further teaching of the invention at least one displacement cylinder is provided. Preferred is the use of a single-piston system in which the displacement cylinder is capable of being pressurised pneumatically. The constructional effort in the case of a single displacement cylinder engaging centrally is distinctly lower than that of two or more pistons operating in parallel, by reason of the problems of synchronisation.

Finally, with a view to sealing the die plate on the opening in the top of the prilling tower, a contact cylinder is provided which is preferably capable of being pressurised hydraulically. With such a contact cylinder the die plate that is active in the given case is pressed onto the opening in the top of the prilling tower with a pressure of preferably 200 bar. Sealing of the die plate is effected on the product side via an O-ring seal, made of Viton B for example, and on the gas side towards the prilling head by metallic means.

The invention is elucidated in more detail below on the basis of preferred embodiments, with reference to drawing FIGS. 1, 2 and 3.

Figure 1:
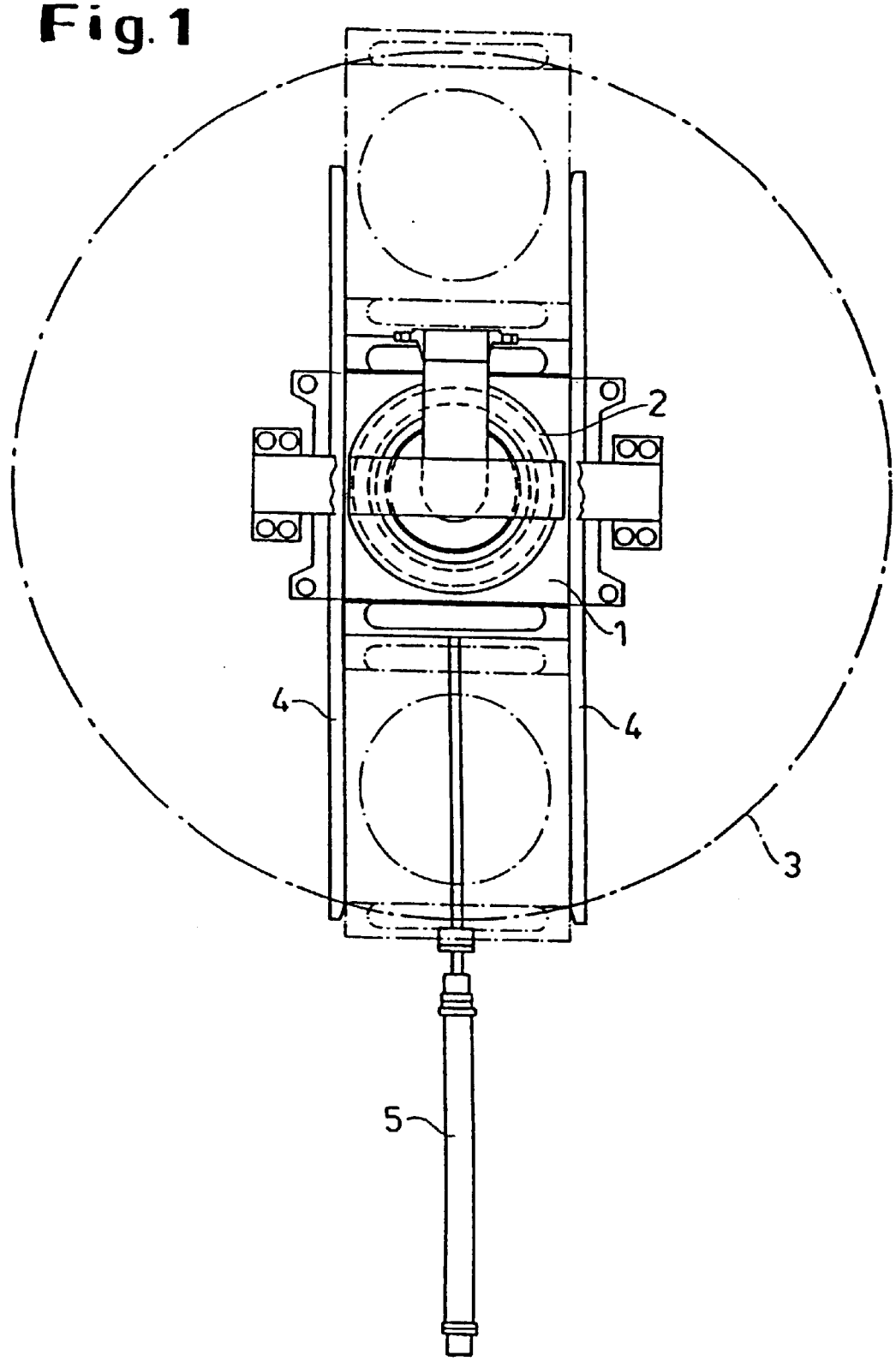
FIG. 1 is representative of a first embodiment of the die-exchanging device according to the invention in top-down view.

The device according to the invention for exchanging a die plate 1 of a prilling tower is shown in FIG. 1, the die plate 1 comprising a die 2 consisting of concentrically arranged bores (only represented schematically), which in the operating position of the die plate 1 is located centrally above the opening, which is not represented, of a prilling tower 3 which is only indicated schematically.

Now, in accordance with the invention, several die plates 1 are provided which are capable of being brought in linear manner along a guide into an operating position or an exchange position by means of a suitable drive mechanism. To this end, slide rails 4 are provided as a guide, which in the embodiment example represented have approximately 2½ times the length of a die plate 1. As already stated, the slide rails 4 exhibit a surface made of copper bronze, preferably a $CuSn_8$ alloy. With a view to further facilitating the linear displacement of the die plates 1, the slide rails 4 and/or the die plates 1 are provided, at least in their contact region, with a polished surface which preferably amounts to a depth of roughness of 0.8 µm.

By way of drive mechanism for displacing the die plates 1, use is made of a pneumatically operable displacement cylinder 5 which is arranged in such a way that it is arranged parallel to the slide rails 4 and engages the die plates 1 centrally. With a view to tilt-free guidance of the die plates 1, the slide rails 4 are preferably provided with a substantially U-shaped profile.

Figure 2:
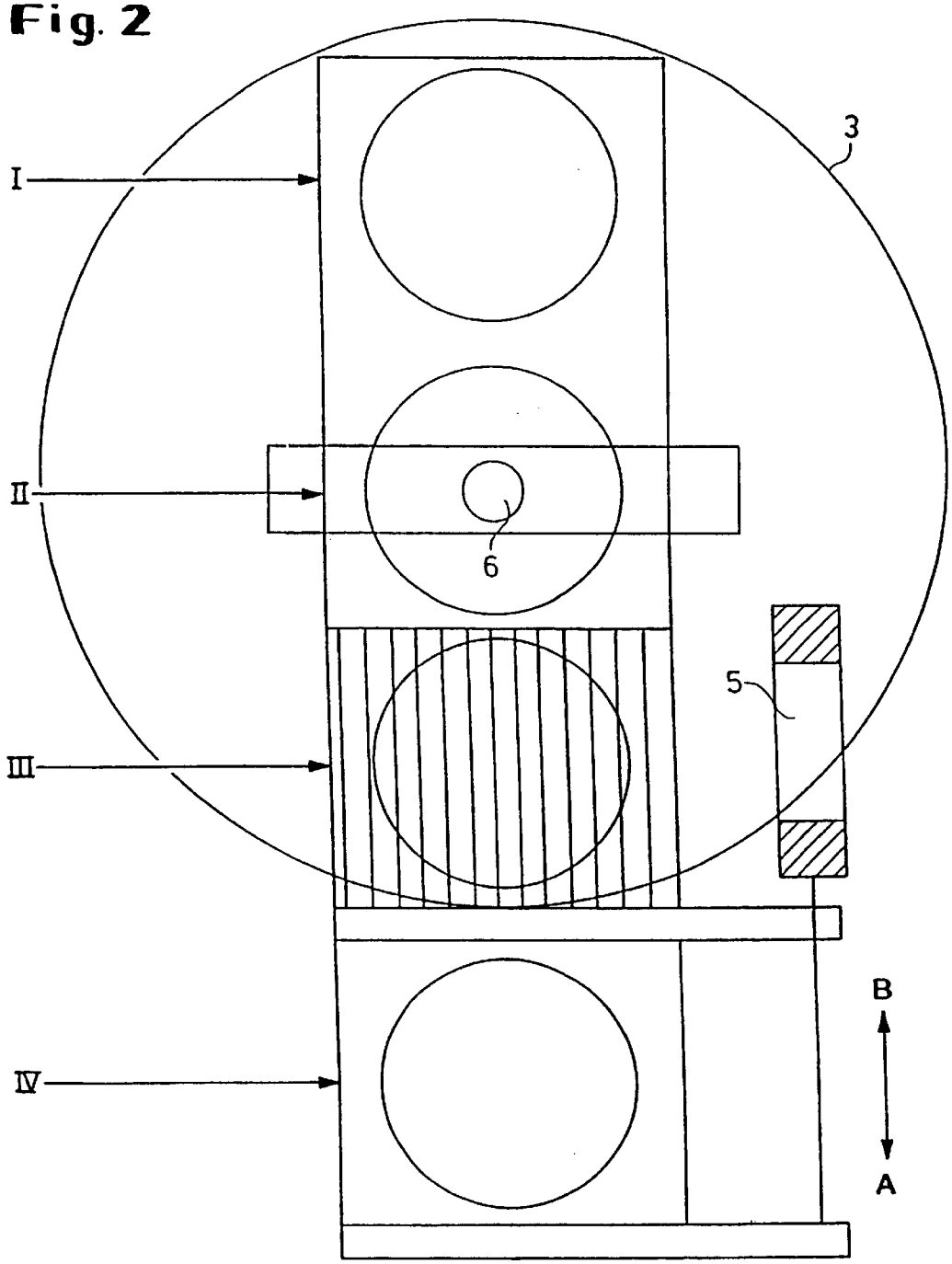
FIG. 2 is schematic representation of a further embodiment of the die-exchanging device.

Now in FIG. 2 a preferred die-exchanging device is represented in which the length of the slide rails 4 amounts to approximately four times the die-plate length. This is particularly preferred for automated operation, since in this way four different positions arise. A cleaned die plate I is firstly brought into position IV (reserve position) and from there is brought by means of the displacement cylinder 5, from position A thereof, into position III (preheating position) by the displacement cylinder moving into position B. Now, after the displacement cylinder has again moved into position A, a new die plate 1 can be inserted which then, again with the aid of the displacement cylinder 5, is brought from the reserve position IV into the preheating position III. In the process the die plate which has been provided for operation and which in the meantime has been preheated moves from position III into position II (operating position). In the operating position the die plate is pressed in sealing manner, by a contact cylinder 6 which is only indicated, into the opening of the prilling tower 3, which is likewise only indicated. With a view to renewed exchange of the die plate, the latter is brought, as previously described, from position II into position I (removal position) after the pressure of the contact cylinder 6 has been removed.

With a view to cleaning, the contaminated die plate 1 can be removed from position I and, after cleaning has taken place, can be transferred again into the reserve position IV.

The entire exchange operation is elucidated in more detail below on the basis of an example which is represented in FIG. 3:

In normal operation of the prilling tower 3 the valves 7 and 8 are switched in such a way that the bisphenol melt is conveyed to the prilling tower 3 in temperature-controlled and quantity-controlled manner by means of a melt pump 9. In this connection the flushings with nitrogen to the die plate 1, that is to say the valve 8, and the recirculation to the melt container 10, that is to say the valve 7, are shut off. The die plate 1, which is only represented schematically, is hydraulically sealed by a contact cylinder, which is not represented here, and by a pressure of 200 bar, on the product side via an O-ring seal made of Viton B and on the gas side towards the prilling tower 3 by metallic means. The pneumatic displacement cylinder 5 (cf. FIG. 2) is in position A. Three die plates are inserted in the device, one in position II (operating position), one in position III (preheating position) and one in position IV (reserve position). The "ejection space" for the die plate to be exchanged (that is to say, position I) is free.

By way of preparation for the exchange of dies, the valve 7 is switched in such a way that the bisphenol melt is rerouted from the prilling tower 3 to the melt container 10. The valve 8 is switched, it closes the path of the melt and simultaneously opens the supply of nitrogen to the prilling tower 3 in order to initiate the $N_2$ flushing. In order that the pipeline between valves 7 and 8 can drain clean, an adjustable timing element is provided for the purpose of switching the valve 8. By switching the valve 8 over, the $N_2$ flushing operation is concluded and the $N_2$ circuit ventilator is switched off. The pressure in the prilling tower 3 is reduced to a $P_0$ of less than 4 mbar by relaxation downstream of the circuit filter.

The actual die-exchange operation is initiated by relieving the load on the hydraulic contact cylinder 6. As soon as the hydraulic pressure has been reduced, the pneumatic displacement cylinder 5 moves from position A into position B and in the process displaces all three die plates 1. In this process the die plate that was previously in operation moves to the free ejection space (from II to I), the preheated die plate 1 moves into the operating position (from III to II) and the reserve plate moves into the preheating zone (from IV to III). As soon as the displacement cylinder 5 has reached position B, the hydraulic contact cylinder 6 is again placed under pressure, so that imperviousness in the region of the die plate 1 is guaranteed. Subsequently the displacement cylinder moves again into its initial position A.

With a view to resuming the operation of the prilling tower, the operating pressure is set to about 50 mbar as a result of a feed of nitrogen $N_2$. Subsequently the nitrogen circuit ventilator is switched in and the hydraulic contact cylinder 6 is pressurised. In the process the pressure of the contact cylinder 6 unlocks the valve 7 which has to be switched over for the purpose of resuming the operation of the prilling tower 3. After the operating speed of the ventilator has been attained, the supply of melt to the prilling tower 3 is enabled by switching the valve 7. Prilling of the bisphenol melt now takes place automatically, corresponding to the predetermined quantity and the selected die plate 1, in a range from 500 to 8,000 kg/h.

With a view to cleaning the die plates 1, the latter are cleaned after operation in an ultrasound bath in dilute caustic-soda solution (6.5% NaOH) at ambient temperatures for about 30 min. After this, the die plates 1 are vigorously rinsed with fully de-ionized water and are dried prior to re-use.

What is claimed is:

1. A device for exchanging a die plate of a molten bisphenol A prilling tower, said device comprising at least two die plates which are capable of being brought in a linear manner along a guide into an operating position (II) or an exchange position (I) by means of a drive mechanism, wherein said prilling tower has a top having an opening therein, said device further comprising at least one contact cylinder, said contact cylinder holding reversibly said die plate over the opening in the top of the prilling tower and in said operating position (II).

2. The device of claim 1 wherein slide rails having a length of at least twice the die-plate length are provided as a guide for said die-plate.

3. The device of claim 2 wherein the slide rails have a length of four times the die-plate length.

4. The device of claim 2 wherein the surface of the slide rails consists of copper bronze.

5. The device of claim 4 wherein the surface of the slide rails consists of $CuSn_8$ alloy.

6. The device of claim 2 wherein at least one of the slide rails and the die plates have a polished surface on their contact region.

7. The device of claim 6 wherein the depth of roughness of the polished surfaces amounts to 0.8 µm.

8. The device of claim 1 wherein said drive mechanism comprises at least one displacement cylinder for displacing the die plate.

9. The device of claim 8 wherein said displacement cylinder comprises a single-piston system which is capable of being pressurized pneumatically.

10. The device of claim 1 wherein the contact cylinder is reversibly pressurized hydraulically.

11. A process for the automated operation of the device of claim 1 comprising:

(a) redirecting a bisphenol melt from the prilling tower into a melt container;

(b) feeding nitrogen into the prilling tower over a predetermined period of time;

(c) relaxing the pressure in the prilling tower;

(d) releasing the contact cylinder from the die plate;

(e) actuating the drive mechanism and displacing said die plate from the exchange position into the operating position;

(f) applying the contact cylinder onto the die plate in the operating position;

(g) feeding nitrogen into the prilling tower over a predetermined period of time; and (h) redirecting the bisphenol melt from the melt container back into the prilling tower through said die plate in said operating position.

12. The process of claim 11 wherein the die plate is selected to handle load ranges from 0.5 to 0.8 tons of bisphenol A melt per hour, and said contact cylinder holds said die plate in said operating position under an initial contact pressure of from 0.1 to 0.3 bar.

* * * * *